United States Patent
Craddock et al.

(10) Patent No.: US 10,698,131 B2
(45) Date of Patent: Jun. 30, 2020

(54) METHODS FOR IMPROVING MATRIX DENSITY AND POROSITY ESTIMATES IN SUBSURFACE FORMATIONS

(71) Applicant: SCHLUMBERGER TECHNOLOGY CORPORATION, Sugar Land, TX (US)

(72) Inventors: Paul Ryan Craddock, Scituate, MA (US); Andrew Pomerantz, Lexington, MA (US); Frank Shray, Littleton, CO (US)

(73) Assignee: Schlumberger Technology Corporation, Sugar Land, TX (US)

( * ) Notice: Subject to any disclaimer, the term of this patent is extended or adjusted under 35 U.S.C. 154(b) by 157 days.

(21) Appl. No.: 15/053,604

(22) Filed: Feb. 25, 2016

(65) Prior Publication Data

US 2017/0248011 A1 Aug. 31, 2017

(51) Int. Cl.
*G01V 8/10* (2006.01)
*G01N 9/36* (2006.01)
(Continued)

(52) U.S. Cl.
CPC ............... *G01V 8/10* (2013.01); *G01N 9/36* (2013.01); *G01N 15/088* (2013.01); *G01N 21/35* (2013.01);
(Continued)

(58) Field of Classification Search
CPC ... G01N 9/36; G01V 5/04; G01V 8/10; G01V 2210/6163; G01V 2210/6167;
(Continued)

(56) References Cited

U.S. PATENT DOCUMENTS

| 4,149,805 A | 4/1979 | Chew, III |
| 4,321,465 A | 3/1982 | Stover et al. |

(Continued)

OTHER PUBLICATIONS

Alfred, D. et al., "A New Petrophysical Model for Organic Shales", Proceedings of the SPWLA 53rd Annual Logging Symposium, Cartagena, Colombia, 2012, 15 pages.
(Continued)

*Primary Examiner* — Mouloucoulaye Inoussa
(74) *Attorney, Agent, or Firm* — Bridget Laffey

(57) ABSTRACT

Methods may include estimating the weight fractions of kerogen and inorganic mineral components of at least an interval of a subsurface formation; determining the grain density of kerogen and inorganic mineral components, wherein at least the grain density of kerogen is determined by one or more infrared measurements; and calculating the formation matrix density of at least an interval of the subsurface formation from the estimated weight fractions and the determined grain density. In another aspect, methods may include estimating the weight fractions of kerogen and inorganic mineral components of at least an interval of a subsurface formation; determining the grain density of kerogen and inorganic mineral components, wherein at least the grain density of kerogen is determined by one or more infrared measurements; and calculating the formation matrix density of at least an interval of the subsurface formation from the estimated weight fractions and the determined grain density; calculating the bulk density for at least an interval of the subsurface formation; and determining the total porosity of at least an interval of the subsurface formation as a function of depth by combining the calculated formation matrix density and the calculated bulk density.

21 Claims, 11 Drawing Sheets

(51) Int. Cl.
*G01V 5/04* (2006.01)
*G01N 15/08* (2006.01)
*G01N 33/24* (2006.01)
*G01N 21/3563* (2014.01)
*G01N 21/35* (2014.01)
*G01N 21/552* (2014.01)

(52) U.S. Cl.
CPC ....... *G01N 21/3563* (2013.01); *G01N 33/241* (2013.01); *G01V 5/04* (2013.01); *G01N 21/552* (2013.01); *G01N 2021/3595* (2013.01)

(58) Field of Classification Search
CPC .... E21B 49/088; E21B 21/066; E21B 49/005; E21B 43/26
USPC ............................ 702/11; 175/58; 250/269.6
See application file for complete search history.

(56) References Cited

U.S. PATENT DOCUMENTS

| | | | | |
|---|---|---|---|---|
| 4,645,927 | A | * | 2/1987 | Ellis ....................... G01V 5/101 250/264 |
| 4,722,220 | A | | 2/1988 | Herron |
| 4,903,527 | A | | 2/1990 | Herron |
| 5,741,707 | A | | 4/1998 | Herron et al. |
| 8,906,690 | B2 | | 12/2014 | Pomerantz |
| 2002/0136680 | A1 | * | 9/2002 | Kanno ................. C04B 38/0022 423/445 R |
| 2009/0053417 | A1 | * | 2/2009 | Mino ..................... B05D 1/185 427/265 |
| 2009/0254283 | A1 | * | 10/2009 | Jacobi ................... G01V 11/00 702/11 |
| 2013/0269420 | A1 | * | 10/2013 | Valenza, II .......... G01N 15/088 73/38 |
| 2013/0269933 | A1 | | 10/2013 | Pomerantz et al. |
| 2013/0270011 | A1 | * | 10/2013 | Akkurt .................. E21B 49/088 175/58 |
| 2013/0273661 | A1 | * | 10/2013 | Pomerantz ......... G01N 21/3563 436/29 |

OTHER PUBLICATIONS

Charsky, A. et al., "Quantitative Analysis of Kerogen Content and Mineralogy in Shale Cuttings by Diffuse Reflectance Infrared Fourier Transform Spectroscopy", Paper SCA2012-27, Proceedings of the 2012 Society of Core Analysts Annual Meeting, Aberdeen, Scotland, 12 pages.
Gardner, G.H.F. et al., "Formation Velocity and Density—the Diagnostic Basics for Stratigraphic Traps", Geophysics, 1974, 39(6), pp. 770-780.
Herron, M. M. et al., "Kerogen Content and Maturity, Mineralogy and Clay Typing from DRIFTS Analysis of Cuttings or Core", Proceedings of the SPWLA 55TH Annual Logging Symposium, Abu Dhabi, United Arab Emirates, 2014, 14 pages.
Okiongbo, K. S., et al., "Changes in Type II Kerogen Density as a Function of Maturity: Evidence from the Kimmeridge Clay Formation", Energy & Fuels, 2005, 19, pp. 2495-2499.
Passey, Q. R. et al., "A Practical Model for Organic Richness from Porosity and Resistivity Logs", AAPG Bulletin, 1990, 74(12), pp. 1777-1794.
Schmoker, J. W., "Determination of Organic Content of Appalachian Devonian Shales from Formation—Density Logs: Geologic Notes", AAPG Bulletin, 1979, 63(9), pp. 1504-1509.
Schmoker, J. W. et al., "Organic Carbon in Bakken Formation, United States Portion of Williston Basin", AAPG Bulletin, 1983, 67(12), pp. 2165-2174.
Ward, J.A ., "Kerogen Density in the Marcellus Shale", SPE-131767, presented at the SPE Unconventional Gas Conference, Pittsburgh, Pennsylvania, USA, 2010, 4 pages.
Mavko, G. et al., "Empirical Relations" in The Rock Physics Handbook—Tools for Seismic Analysis of Porous Media, Second Edition, Cambridge University Press, 2009, Chapter 7, 56 pages.
Castagna, J. P. et al., "Rock Physics—The Link Between Rock Properties and AVO Response", in Offset-Dependent Reflectivity—Theory and Practice of AVO Analysis, ed. J.P. Castagna and M. Bachus, Investigations in Geophysics, No. 8, Society of Exploration Geophysicists, Tulsa, Oklahoma, 1993, pp. 135-171.
Herron, M.M. et al, "Log Interpretation Parameters Determined from Chemistry, Mineralogy and Nuclear Forward Modeling", Paper SCA-9727, Proceedings of the Society of Core Analysts 1997 International Symposium, Calgary, AB, Canada, 12 pages.
Herron, S.L. et al., Application of nuclear spectroscopy logs to the derivation of formation matrix density, Transactions of the SPWLA 41st Annual Logging Symposium, Jun. 4-7, 2000, Dallas, Texas, USA, 12 pages.
Rosen, et al., "Universally Applicable Model for the Quantitative Determination of Lake Sediment Composition Using Fourier Transform Infrared Spectroscopy", Environmental Science & Technology, Ameican Chemical Society, (2011) vol. 45, pp. 8858-8865.
Washburn, et al, "Multivariate Analysis of ATR-FTIR Spectra for Assessment of Oil Shale Organic Geochemical Properties", Organic Geochemistry, vol. 63 (2013), 7 pages.
Painter, et al, "Concerning the Application of FT-IR to the Study of Coal: A Critical Assessment of Band Assignments and the Application of Spectral Analysis Programs", Applied Spectroscopy, vol. 35, No. 5, (1981), pp. 475-485.
Lis, et al, "FTIR Absorption Indices for Thermal Maturity in Comparison with Vitrinite Reflectance R0 in Type-II Kerogens from Devonian Black Shales", Organic Chemistry, vol. 36, (2005) pp. 1533-1552.

* cited by examiner of the claimed subject matter, nor is it intended to be used as an aid in limiting the scope of the claimed subject matter.

METHODS FOR IMPROVING MATRIX DENSITY AND POROSITY ESTIMATES IN SUBSURFACE FORMATIONS

BACKGROUND

Porosity is one of the important parameters in petrophysical evaluations of petroleum reservoirs, and is defined as the interconnected pore volume or void space in a rock that contributes to fluid flow or permeability in a reservoir. Porosity describes the pore volume that exists in a geological formation and is important to petroleum engineers, because pore networks may contain economically-valuable hydrocarbons, and is a useful measure in estimating potential petroleum reserves. Types of porosity measurements include effective porosity, which excludes isolated pores and pore volume occupied by water adsorbed on clay minerals or other grains, and total porosity, which is the total void space in the rock whether or not it contributes to fluid flow. Porosity may also be used to determine permeability of the formation, which may provide estimates of production rates, the location of completion and perforation intervals, and potential injection behavior and patterns.

A number of methods exist for measuring porosity, including calculating porosity from bulk density and grain density on core samples taken from a selected formation. Analytical measurement techniques used to determine porosity may include gas saturation with pressure-volume control, liquid saturation with weighting, and petrographic analysis of thin sections. However, such methods of formation evaluation are disadvantageous in that they are relatively time-consuming, complex, may require intact core samples, and are better suited for laboratory analysis rather than use in the field.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, methods in accordance with the present disclosure may include estimating the weight fractions of kerogen and inorganic mineral components of at least an interval of a subsurface formation; determining the grain density of kerogen and inorganic mineral components, wherein at least the grain density of kerogen is determined by one or more infrared measurements; and calculating the formation matrix density of at least an interval of the subsurface formation from the estimated weight fractions and the determined grain density.

In another aspect, methods in accordance with the present disclosure may include estimating the weight fractions of kerogen and inorganic mineral components of at least an interval of a subsurface formation; determining the grain density of kerogen and inorganic mineral components, wherein at least the grain density of kerogen is determined by one or more infrared measurements; and calculating the formation matrix density of at least an interval of the subsurface formation from the estimated weight fractions and the determined grain density; calculating the bulk density for at least an interval of the subsurface formation; and determining the total porosity of at least an interval of the subsurface formation as a function of depth by combining the calculated formation matrix density and the calculated bulk density.

Other aspects and advantages of the invention will be apparent from the following description and the appended claims.

DETAILED DESCRIPTION

Figure 1:
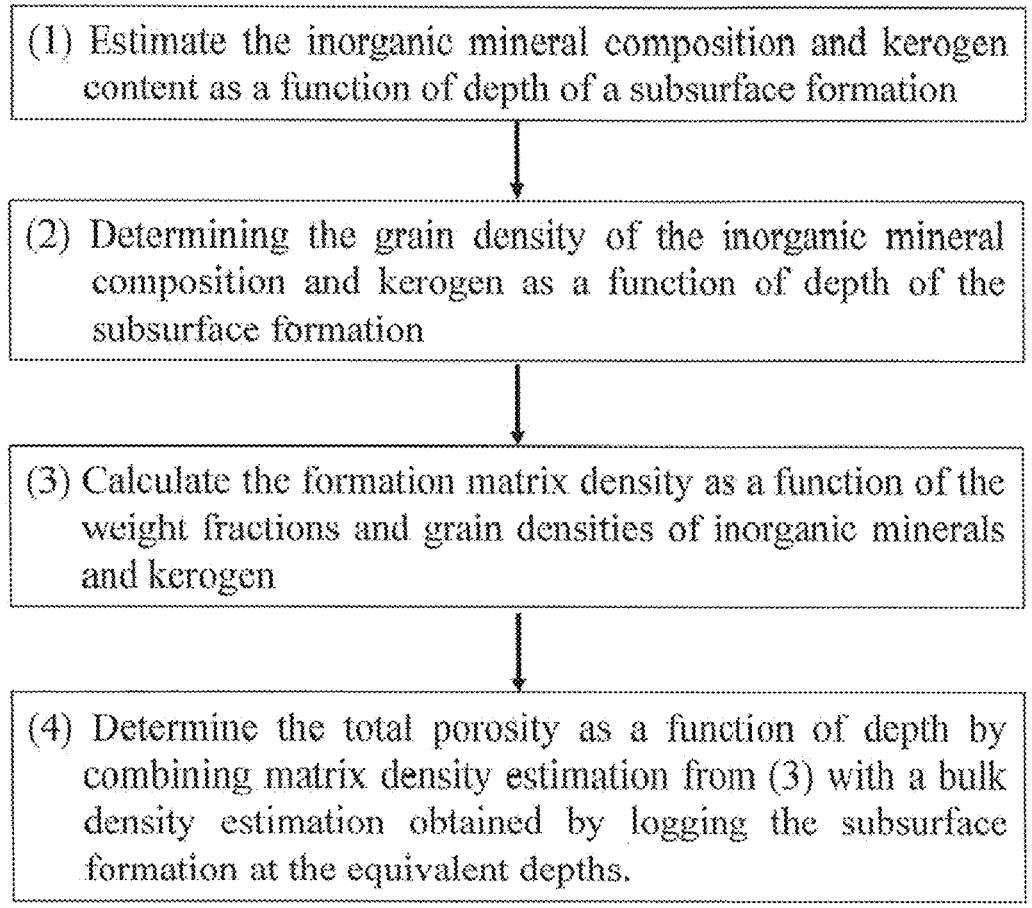
FIG. 1 is an embodiment of a workflow for determining formation porosity in accordance with the present disclosure.

Embodiments of the present disclosure are directed to methods of determining total porosity as a function of depth for a subsurface formation, which may correct for uncertainty that occurs when measuring formations containing kerogen and other organic solids. In one or more embodiments, methods in accordance with the present disclosure may include estimating the total porosity of subsurface formations from the matrix density of the formation that may be derived from the determination of the solid fractions of inorganic matrix minerals and kerogen. In some embodiments, methods may also combine matrix density measurements with estimates of bulk density determined from a number of well logging techniques in order to develop a log of total porosity as a function of depth.

Reservoir evaluation is an important part of hydrocarbon exploration and extraction. During evaluation, formation parameters such as permeability, porosity, and the presence and/or amount of hydrocarbons are studied to determine the economic viability of the play and, in some cases, the order in which production of formation intervals should be initiated. Permeability is the measure of a rock's ability to allow fluids to pass through it. Porosity is the volumetric void space in the rock that is not occupied by solid materials. Porosity is often difficult to estimate in organic-rich source rocks and unconventional reservoirs due to anomalous responses of logging tools to the presence of solid organic matter in a formation. For example, some wellbore tools exhibit increased apparent porosity in response to the presence of organic matter in the formation, such as when sonic log measurements record low velocity when passing over a formation rich in organic matter. Similarly, neutron logs measuring the high hydrogen content of organic matter may give erroneous estimates for apparent porosity.

Subsurface formations including unconventional formations may contain inorganic minerals as well as solid organic matter, referred to as kerogen, which forms part of the solid rock matrix. As used herein, "kerogen" is defined as any solid organic matter, such as heavy hydrocarbons derived from plant and bacterial remains, that is dispersed in sedimentary rocks, solid under standard temperature and pressure, and insoluble in organic solvents such as chloroform or polarizable solvents such as benzene and carbon tetrachloride. By way of contrast, bitumen is defined as the fraction of organic matter that is soluble in organic solvent.

Methods in accordance with the present disclosure may be used to develop improved matrix density and total porosity estimates in a subsurface formation by solving for the concentration of matrix minerals and kerogen as a function of depth in a formation. In some embodiments, matrix density and total porosity estimates may also account for variations in the grain density of solid organic materials such as kerogen in the formation. The "matrix" of a formation refers to any and all solid components in the formation, including inorganic minerals and kerogen, while "matrix density" refers to the density of the solid matrix alone, excluding porosity. "Grain density" is the calculated density of a particular matrix component that excludes porosity. For solid organic materials, grain density is known to change with thermal maturity, which is the degree of heating a source rock has undergone and a measure of the completeness of the transformation of kerogen into hydrocarbon. Thermal maturity may be evaluated in some embodiments by measuring vitrinite reflectance or by pyrolysis of a sample from a given petroleum reservoir.

In one aspect, methods in accordance with the present disclosure are directed to quantifying the matrix density and porosity of subsurface formations in which kerogen is a measurable portion of the solid rock matrix. Kerogen is solid amorphous organic matter that does not possess a regularly defined crystallographic structure and is not amenable to quantification in geological samples by x-ray diffraction methods. However, kerogen interacts with infrared (IR) radiation, which may be used to quantify the kerogen content and density in organic-rich geological formations. In one or more embodiments, determination of matrix density may include using a transform that quantifies kerogen grain density as a function of the kerogen-dependent signature of a geological sample obtained using IR spectroscopy. In some embodiments, IR spectroscopy methods may be used to determine, from a single measurement, formation mineralogy, mineral fraction of formation by weight, kerogen fraction of formation by weight, and kerogen grain density, which may then be used to compute overall matrix density and/or combined with one or more inputs to compute total porosity.

In one or more embodiments, methods in accordance with the present disclosure may use diffuse reflectance IR Fourier transform spectroscopy (DRIFTS) to solve for mineral content, kerogen content, and kerogen grain density, which may be used to compute matrix density. When employed as a logging technique, DRIFTS may enable a single measurement estimation of inorganic mineralogy, kerogen content, and kerogen grain density in geological samples from every depth in a subsurface formation. In addition to determining the weight fraction and grain density of kerogen, DRIFTS may be used to determine the inorganic mineralogy of a formation sample in some embodiments. Common inorganic minerals in sedimentary rocks for which DRIFTS solves include, but are not limited to, quartz, feldspar, calcite, dolomite, illite, smectite, kaolinite, chlorite, muscovite, anhydrite.

In one or more embodiments, matrix density calculated using methods in accordance with the present disclosure may be combined with bulk density in some embodiments to calculate total porosity. Bulk density is a measure of the average density of the measured formation, while matrix density considers the solid fraction of the measured sample, and total porosity describes the percentage of pore volume or void volume within the rock that can contain fluids. Total porosity is computed from the matrix density and bulk density, which are often obtained separately using, for example, laboratory analysis in combination with a density logging tools, or other techniques. However, in some embodiments, density measurements may be obtained by converting information from other domains such as velocity through known physical relationships.

Methods in accordance with the present disclosure may include obtaining matrix density, bulk density, and total porosity from cuttings and density logs, and may be applied in both vertical and horizontal wells to evaluate potential hydrocarbon-bearing reservoirs. In some embodiments, drill cuttings retrieved from a wellbore are representative of the reservoir rock and may be recovered in real-time, which is often referred to as "mud logging" or "cuttings evaluation," and used to generate a log of formation parameters as a measure of depth. Cuttings may also be processed prior to measurement in some embodiments by removing residual drilling fluids that can increase measurement error depending on wellbore fluid composition.

This paragraph will introduce each of the components that may be used in methods in accordance with the present disclosure and the sections that follow will discuss each of the respective method components in greater detail. With particular respect to FIG. 1, a flowchart depicts an embodiment of a method in accordance with the present disclosure. Initially, formation composition is determined at (1) by estimating the individual contributions of the inorganic mineral composition and kerogen in a formation sample. Next, the grain density of the inorganic mineral composition and kerogen in the formation sample is calculated at (2). At (3), the formation matrix density as a function of the weight fractions for each of the inorganic mineral composition and kerogen is determined from the weight fractions and grain densities for the inorganic mineral composition and kerogen determined in (1) and (2). The total porosity of the formation as a function of depth is then determined in (4) by combining matrix density estimation from (3) with bulk density estimates.

Determining Matrix Composition

Methods in accordance with the present disclosure may include determining a quantitative estimate of the weight fraction of the various solid matrix components of a formation, such as the weight fractions of the inorganic mineral components and kerogen. In some embodiments, methods may include determining the weight fraction of matrix components as a function of depth in a subsurface formation. Matrix composition measurements in accordance with the present disclosure may be performed on representative samples of the subsurface formation that may include drill cuttings, core samples, thin sections, wellbore tool logging measurements, and the like, from vertical and horizontal wells.

In one or more embodiments, methods may be used to compute inorganic mineralogy and kerogen content from the IR spectrum of a sample using Diffuse Reflectance Infrared Fourier Transform Spectroscopy (DRIFTS). Further, DRIFTS may be used to estimate the grain density of kerogen in some embodiments. While some methods of petrophysical characterization may be performed on formation sampling and cores, methods in accordance with the present disclosure may also be applied where core samples do not exist or cannot be obtained, such as from horizontal wells, and in formations with and without kerogen. In some embodiments, IR spectroscopy techniques in accordance with the present disclosure may also include other IR techniques such as attenuated total reflection, transmission Fourier transform infrared spectroscopy, and other techniques that may be adapted to measure the concentration of inorganic and hydrocarbon matrix components based on IR absorbance.

Methods in accordance with the present disclosure may also integrate additional physics and measurements with the DRIFTS measurement in order to improve the accuracy of existing DRIFTS mineralogy interpretations or to provide quantification of additional minerals that can be used in the matrix density computation. Examples include, but are not limited to, X-ray diffraction, attenuated total reflection spectroscopy (ATR), Transmission Fourier transform infrared spectroscopy (FTIR), as well as elemental measurements such as from X-ray fluorescence (XRF), mass spectrometry, LECO combustion analysis, and coulometry.

One example of formation mineralogy characterization for illustrative purposes is the determination of pyrite content of a formation from a sulfur elemental analysis. The mass abundance of pyrite is equal to the mass abundance of sulfur in pyrite divided by the well-known mass stoichiometric coefficient 0.5345 (sulfur in pyrite is 53.45%). Any number of petrophysical interpretations known to those skilled in the art may be used to interpret elemental concentrations with respect to mineral concentrations. Pyrite is illustrated here because pyrite is a dense mineral phase ($\rho$=5.0 g/cm$^3$) and its inclusion is beneficial in any formation hosting pyrite for a more accurate matrix density estimate, and resulting porosity estimate.

Determining Kerogen Grain Density

In addition to determining the weight fractions of matrix components, methods in accordance with the present disclosure may include determining the kerogen grain density and/or kerogen grain density as a function of depth in a subsurface formation. In hydrocarbon reservoirs, reservoir quality assessment may involve the determination of kerogen content and the kerogen thermal maturity. Thermal maturity may be used to determine the grain density exhibited by the weight fraction of kerogen in a formation sample. For example, while most assessment methods assume a constant value of 1.2 g/cm$^3$ for the grain density of kerogen, the actual value may range from at least 1.05 to 1.51 g/cm$^3$ and higher with increasing thermal maturity. Variations in thermal maturity and kerogen grain density may then produce inconsistent and erroneous values for matrix density if the assumed value for kerogen grain density is used for kerogen-rich formations, including unconventional reservoirs such as shales, which can lead to erroneous estimates of the true matrix density and, in turn, under- or over-estimation of the hydrocarbon content of the formation.

In some embodiments, estimation of grain density for kerogen may include determining the thermal maturity of a formation using vitrinite reflectance which measures the percentage of incident light reflected form the surface of vitrinite particles in a sedimentary rock. Vitrinite reflectance originated as a method of ranking the maturity of coals, but has evolved as a method of determining whether a formation sample could be regarded as a source rock capable of producing various hydrocarbons. During testing, the reflectivity of individual grains of vitrinite from a rock sample are measured under a microscope. The measurement is given in units of reflectance, % $R_o$, with typical values ranging from 0% $R_o$ to 3% $R_o$, with values for gas-generating source rocks typically exceeding 1.5%. Other methods of determining kerogen grain density may include isolation and testing of cores using various laboratory techniques, example, Rock-Eval $T_{max}$ analysis, which looks at the maximum rate of hydrocarbon generation that occurs during pyrolysis of a kerogen-containing sample. However, these grain density measurement techniques may have limited use because the measurements are time-consuming to collect, often difficult to interpret, and poorly suited for use in the field.

In one or more embodiments, the grain density of kerogen in a subsurface formation may be calculated by using the relationship between kerogen grain density and the response of an IR tool measurement or log in order to calculate the kerogen grain density without the requirement of the intermediate step of determining thermal maturity for a given formation sample. In some embodiments, an IR lineshape obtained from analysis of a formation sample may be used to estimate kerogen grain density, in addition to the kerogen volume fraction and other formation parameters. For example, IR lineshapes may be derived using IR techniques that include DRIFTS, attenuated total reflection spectroscopy, and transmission Fourier transform infrared spectroscopy (FTIR).

In one or more embodiments, kerogen grain density may be calculated directly from an IR spectrum of a formation sample or wellbore log measured by IR techniques such as DRIFTS. The IR spectrum in the wavenumber range of 2000 to 3500 cm$^{-1}$ is characteristic of various forms of carbon-hydrogen bond stretching and, in the context of formation characterization, may be a measure of the content of kerogen and other hydrocarbons. Further, this region of the IR spectrum changes systematically with thermal maturity and comparing the ratio of various stretching modes may provide insight on the relative concentration of saturated hydrocarbons with unsaturated and aromatic carbons and, in effect, the degree of conversion of kerogen to bitumen and petroleum.

In one or more embodiments, kerogen grain density may be determined by solving the DRIFTS IR spectrum lineshape as a ratio of the IR absorbance arising from asymmetric CH$_3$ and CH$_2$ stretches at wavenumbers centered around 2957 and 2925 cm$^{-1}$, respectively, because this ratio varies systematically with thermal maturity. In some embodiments, IR wavenumber ratios may be obtained from quantifying the IR absorbance arising from symmetric CH$_3$ and CH$_2$ stretches at wavenumbers centered around 2857 and 2872 cm$^{-1}$. IR wavenumber ratios may also include the ratio of the total aliphatic C—H IR absorbance between 2800 and 3000 cm$^{-1}$ and the total aromatic C—H IR absorbance between 3000 and 3100 cm$^{-1}$. While a limited number of examples of IR spectrum ratios are presented, it is envisioned that any spectrum ratios that correlate to varying levels of kerogen thermal maturity may be incorporated into methods in accordance with the present disclosure. Correlations between kerogen grain density and IR spectra lineshape in accordance with the present disclosure may be quantified and optimized using any number of techniques such as linear regression, multiple-linear regression, non-linear regression, exponential regression, logarithmic regression, etc.

In one or more embodiments, mineralogy and kerogen content determined by DRIFTS may then be combined in some embodiments with kerogen grain density and mineral grain density to generate sufficient information to compute matrix density without relying on assumptions that may introduce error. For example, correlating between the DRIFTS IR spectrum lineshape and kerogen grain density may reduce the need to calibrate against independent measures of thermal maturity such as $T_{max}$, or relying on assumed values for kerogen grain density that are known to introduce a degree of analytical uncertainty. In some embodiments, DRIFTS measurements may be calibrated by comparing mineralogy calculations with FTIR, XRD, XRF or similar techniques, and the kerogen calculation may be calibrated against LECO total organic carbon to verify the organic matter content and kerogen amount.

Determining Formation Matrix Density

Methods in accordance with the present disclosure may involve using the weight fractions of the formation components and their respective grain densities to compute the formation matrix density. In some embodiments, DRIFTS measurements may be used to compute one or more of the weight fractions for the formation components, along with the calculated grain densities, in order to determine matrix density for a given formation. DRIFTS data may also be used to generate a log of matrix density as a function of depth in a formation and/or combined with bulk density estimates such as from a density log to provide a more accurate estimate of total porosity in organic-rich subsurface formations. Matrix density calculations in accordance with the present disclosure may account for the variation in kerogen density and allow for improved calculation of the void component of the matrix and, consequently, improved estimates of petrophysical characteristics such as kerogen grain density, matrix density, porosity, and other density dependent measurements.

In one or more embodiments, matrix density may be calculated from quantitative mineralogy by determining the weight fractions and grain densities of all matrix components in the rock formation. In some embodiments, weight fractions and grain density of matrix components may be estimated from similar formation types or by relying on standard values. For example, the grain densities of inorganic minerals, such as quartz, calcite, and dolomite, are known and vary little from formation to formation, and may be applied when determining matrix density for reservoir rocks containing no or negligible amounts of kerogen. However, for those subsurface formations that also contain source rocks having high molecular weight organic materials, the grain density of kerogen may vary between formations depending on the thermal maturity of the kerogen, which can introduce errors that propagate in the computation of matrix density and formation porosity.

Methods in accordance with the present disclosure may include calculating the formation matrix density from the weight fractions of inorganic minerals and kerogen in the sample, divided by their respective grain densities, including the estimated kerogen grain density. In one or more embodiments, matrix density $\rho_{ma}$ may be computed from quantitative mineralogy as a sum of the mineral concentrations weighted by their respective grain densities, which may be expressed as shown in Eq. 1, where $M_i$ is the weight fraction of each matrix component i, and $\rho_{gi}$ is the associated grain density for the component.

$$\frac{1}{\rho_{ma}} = \sum_{i=1} \frac{M_i}{\rho_{gi}} \qquad (1)$$

Methods in accordance with the present disclosure may also compute matrix density $\rho_{ma}$ from formation elemental concentrations using multiple linear regression models as shown in Eq. 2, where $\alpha$, $\beta$, etc. are empirical coefficients derived from the regression analysis.

$$\rho_{ma} = \alpha + \beta Si + \gamma Ca + \delta Fe + \varepsilon S \qquad (2)$$

In some embodiments, the relationships established in equations (1) and (2) may be used to estimate the matrix density of conventional reservoirs containing solid inorganic minerals and non-matrix fluid components such as oil, gas, and water. However, such approaches become more complex or may fail entirely in unconventional source rocks in which kerogen is a fraction of the solid matrix because of the variability in the density with thermal maturity.

Determining Total Porosity

Methods in accordance with the present disclosure may involve calculating the total porosity as a function of depth in a subsurface formation by combining matrix density estimations with bulk density estimations determined from various well logging techniques such as density measurements obtained from logging sondes, conductivity measurements, nuclear magnetic resonance logging, and the like. In some embodiments, methods of porosity determination may take into account the thermal maturity of kerogen within the formation, which may increase the accuracy of porosity calculations and any other values dependent on kerogen grain density.

In one or more embodiments, calculating the porosity of a subsurface formation may include determining bulk density using various density measuring tools or by constructing a "synthetic" density log model from formation measurements or from other formation parameters converted to the density domain. In some embodiments, bulk density measuring tools may include tools that operate by emitting medium-energy gamma rays into a borehole wall that collide with electrons in the formation, lose energy and scatter after successive collisions. The number of collisions is related to the number of electrons per unit volume, or the electron density. The electron density for most minerals and fluids encountered in oil and gas wells is directly proportional to their bulk density, $\rho_{bulk}$. The bulk density measured by the tool results from the combined effects of the fluid (porosity) and the matrix density $\rho_{ma}$ is used to compute density porosity, $\phi_T$, using the expression provided in Eq. 3, where $\rho_{bulk}$ is the density of the bulk formation and $\rho_{fluid}$ is the density of the bulk fluid in the pore volume that includes contributions from oil, gas, and water.

$$\phi_T = \frac{\rho_{ma} - \rho_{bulk}}{\rho_{ma} - \rho_{fluid}} \qquad (3)$$

In one or more embodiments, $\rho_{bulk}$ may be acquired by laboratory analysis or a suitable wellbore tool such as a density sonde such as from wireline or logging-while-drilling.

While $\rho_{fluid}$ may be determined by measuring every depth in a formation, $\rho_{fluid}$ is commonly taken to be 1.0 g/cm³ for a formation because porosity is least sensitive to uncertainties in $\rho_{fluid}$ (porosity uncertainties typically five percent relative or less). Formation matrix density $\rho_{ma}$ may be computed from element or mineral concentrations, but determination of an accurate $\rho_{ma}$ value requires that the grain density of all inorganic and organic components in the rock matrix be known. Bulk formation density, $\rho_{bulk}$, may be acquired by a density sonde such as from wireline, logging-while-drilling, through-the-bit technologies, or other measurement techniques. While $\rho_{fluid}$ may be assumed to be 1.0 g/cm³ in some embodiments, the value may also be estimated from local calibration measurements, iterative optimization, or other techniques.

In some embodiments, methods may incorporate matrix density, $\rho_{ma}$, from DRIFTS with bulk density, $\rho_{bulk}$, from logging measurements at corresponding depths in a formation to provide a semi-continuous log of total porosity through a subsurface formation. Combining matrix density estimates in accordance with the present disclosure from drill cuttings (or other formation sampling techniques) and bulk density estimates may provide a more accurate wellsite estimate of formation porosity from vertical or horizontal wells.

Bulk density measuring tools in accordance with the present disclosure may include wellbore tools such as wireline, logging-while-drilling, or openhole ThruBit. In some embodiments, bulk density measurements may be performed on core samples or other geological samples representing the subsurface formation such as cuttings, plugs, thin sections, or rock chips and then combined with depth data to generate synthetic bulk density logs.

In one or more embodiments, measurements obtained from cuttings and formation samples may be depth shifted using a correlation log to correct for any depth inconsistencies and enable proper comparison of the measurements with other wellbore logs, such as bulk density obtained from various downhole tools, to estimate porosity. For example, K, Th, and U measurements on cuttings samples using X-ray fluorescence spectroscopy, mass spectrometry, or other geochemical tools, may be used to compute a synthetic gamma ray log to correlate cuttings at particular depths with other log measurements such as measured gamma ray logs, bulk density measurements, and the like. In some embodiments, measurements may be determined using the Schlumberger algorithm: $GR_{matrix}=4\times Th$ [ppm]$+8\times U$ [ppm]$+16\times K$ [wt %]. The synthetic matrix gamma ray log from cuttings may then be correlated to a natural gamma ray log from one or more gamma ray logging sondes to verify the depth correlation of the cuttings matrix density log to a bulk density log. Other measurements used for correlation may include resistivity, acoustic logs, and other correlation logs.

In some embodiments, wellbore tools useful in determining formation parameters may incorporate multiple measurements such as gamma, neutron, litho-density, sonic, resistivity, electron density, dual induction formation resistivity, audio temperature, imaging, and the like, including triple-combo, quad-combo, and platform express technologies.

Methods of determining porosity in accordance with the present disclosure are not necessarily limited to the measurement of formation density as measured by a density logging tool, or logging tool measurements in general. Because the domains of velocity, density, and porosity are interrelated, porosity may be determined using other techniques capable of determining the weight fractions of organic and inorganic phases, grain densities of organic and inorganic phases, and matrix density, or conversion to these parameters based on physical and empirical relationships.

In one example, measurements of velocity may also be used to compute porosity. The matrix density described by Eq. 3 may be transformed into the velocity domain to yield a matrix velocity. Matrix velocity can be combined with any one or more of surface or subsurface estimations of bulk formation wave velocity to estimate formation attributes such as porosity. For example, density porosity may be estimated using the Wyllie time-average equation, where $\phi_T$ represents the density porosity and DT represents delta-t, slowness, the inverse of velocity.

$$\phi_T = \frac{DT_{log} - DT_{ma}}{DT_{fluid} - DT_{ma}} \quad (4)$$

Eq. 4 can be written in terms of velocity as follows in Eq. 5, where $V_p$ represents compressional velocity.

$$\frac{1}{V_P} = \frac{\phi_T}{V_{P-fluid}} + \frac{1-\phi_T}{V_{P-ma}} \quad (5)$$

While one such method is described to derive density porosity from matrix velocity, it is also envisioned that similar relationships for other wave velocities, such as shear velocity, may be used similarly without departing from the scope of the instant disclosure. In some embodiments, relationships between velocity and density may be determined empirically. For example, density may be expressed in velocity units of km/s and density in g/cm³ as $\rho_b \approx 1.741 * V_P^{0.25}$. Methods in accordance with the present disclosure may determine matrix velocity from the surface using seismic methods and/or in the borehole using seismic and acoustic methods in both open hole and cased holes to extract the attributes of density or porosity.

Determination of Additional Formation Parameters

In one or more embodiments, the weight fractions of organic and inorganic matrix components and their respective grain densities may be used to estimate formation parameters other than porosity, such as total organic carbon (TOC). TOC is determined from the empirical relationship between density and TOC described in Eq. 6, where $\rho_{om}$ refers to the density of kerogen, $\rho_b$ refers to bulk density of the formation, and $\rho_{ma}$ refers to matrix density; and $\Phi_{om}$ is the pore volume fraction occupied by kerogen.

$$\Phi_{om} = [\rho_b - 0.9922\rho_{ma} - 0.039]/[\rho_{om} - 1.135\rho_{ma} + 0.675] \quad (6)$$

The weight-percent organic-carbon content (TOC) is related to the $\Phi_{om}$ according to the relationship shown in Eq. 7, where R is the ratio of weight-percent kerogen to weight-percent organic carbon.

$$TOC = \Phi_{om}(100\rho_{om})/(R\rho_b) \quad (7)$$

By substituting for $\Phi_{om}$ using equation 6, equation 7 becomes Eq. 8 that may be solved to determine TOC for the sample.

$$TOC = [(100\rho_{om})(\rho_b - 0.039)]/[(R\rho_b)(\rho_{om} - 1.135\rho_{ma} + 0.675)] \quad (8)$$

While previous methods have calculated TOC using assumed values for kerogen grain density and matrix density, such methods may exhibit systematic error because the values vary with the thermal maturity of the organic phase and the abundance and type of the inorganic matrix minerals. In one or more embodiments, the values of kerogen grain and fixed matrix density may be determined according to methods of the present disclosure, including solving for these parameters at every depth in a formation using IR spectroscopy, and used to obtain a more accurate estimate of TOC.

EXAMPLE

In the following example, a sample of a hydrocarbon-bearing formation is analyzed using a workflow in accordance with the present disclosure to derive the total porosity. Core and cuttings samples from wells in unconventional reservoirs in North and South America were analyzed to determine the concentration of various matrix components such as illite, smectite, kaolinite, and chlorite, in addition to non-clay mineral components and kerogen. The method carried out in this embodiment included: (1) estimating mineral and solid organic content for the sample of subsurface formation, (2) estimating the mineral and/or kerogen grain density, (3) estimating the matrix density, and (4) estimating formation porosity. Each of the method components executed will be discussed in turn below.

(1) Estimation of Mineral and Kerogen Content

A formation sample was analyzed to estimate the weight fractions of inorganic matrix minerals (i.e., the inorganic mineralogy) and the weight fraction of kerogen as a function of formation depth. Analysis was done using DRIFTS on drill cuttings recovered from the subsurface formation and prepared appropriately for IR spectroscopic analysis to clean the cuttings samples of hydrocarbon-based fluids that might otherwise be interpreted by DRIFTS as kerogen. In the following examples, the cuttings were separated from the drilling fluid, washed with a base fluid from the drilling fluid used to generate the cuttings, followed by washing with organic solvents, and dried prior to analysis. However, other cleaning procedures that remove traces of drilling fluids and other contaminants may be used without departing from the scope of the instant disclosure.

Figure 2:
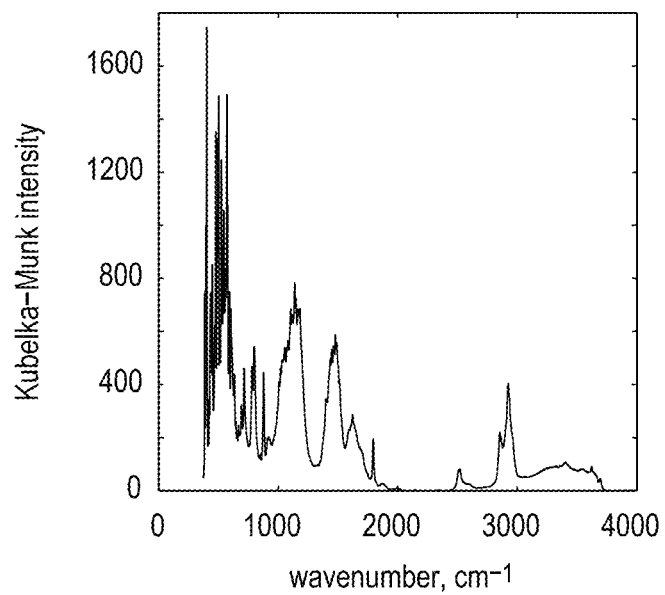
FIG. 2 is a graphical representation depicting the Kubelka-Munk (KM) intensity of light reflection as a function of wavenumber for an unknown formation sample in accordance with methods of the present disclosure.
Figure 3:
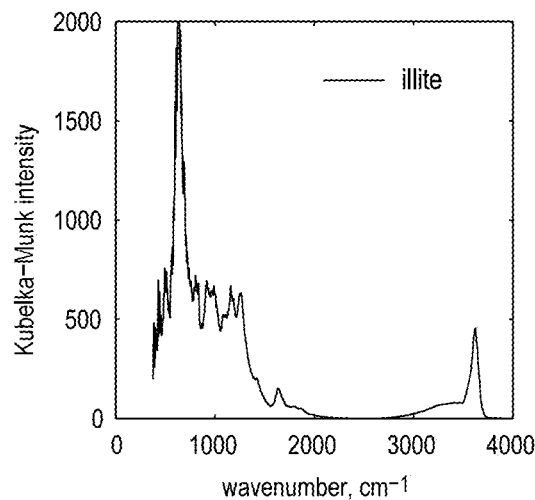
FIG. 3-6 are graphical representations depicting the KM intensity of light reflection as a function of wavenumber for a number of mineral standards in accordance with methods of the present disclosure.
Figure 4:
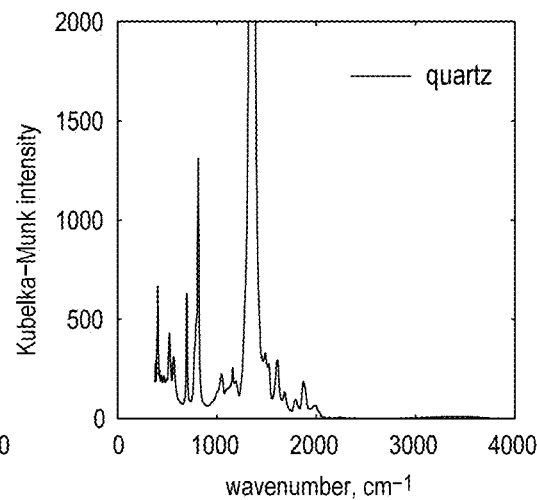
Figure 5:
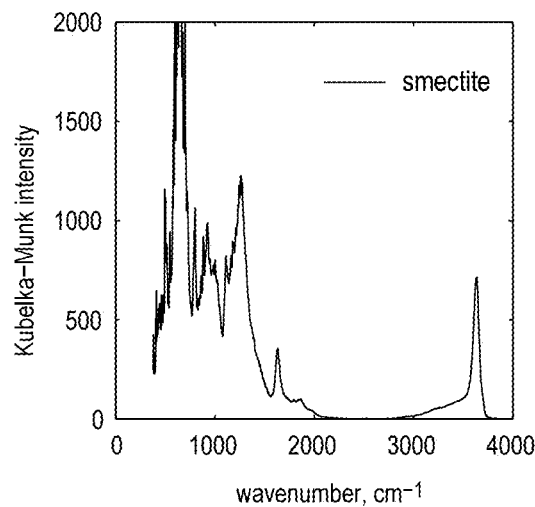
Figure 6:
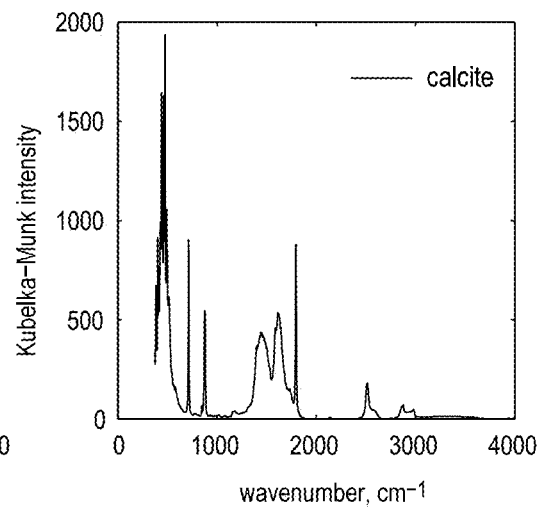

During DRIFTS measurement, a sample was irradiated with infrared light in the mid-IR range between 375 and 4000 cm$^{-1}$ and the intensity of diffusely-reflected light returned to the spectrometer was recorded and collected as Kubelka-Munk (KM) intensity as shown in FIG. 2. KM intensity measurements treat all reflections as occurring along a single direction and are better conditioned than absorbance units for reflection quantification. With particular respect to FIGS. 3-6, the KM spectra were then solved for the respective inorganic matrix mineral concentrations as a weighted linear combination of mineral standard spectra.

(2) Estimation of Kerogen Grain Density

Figure 7:
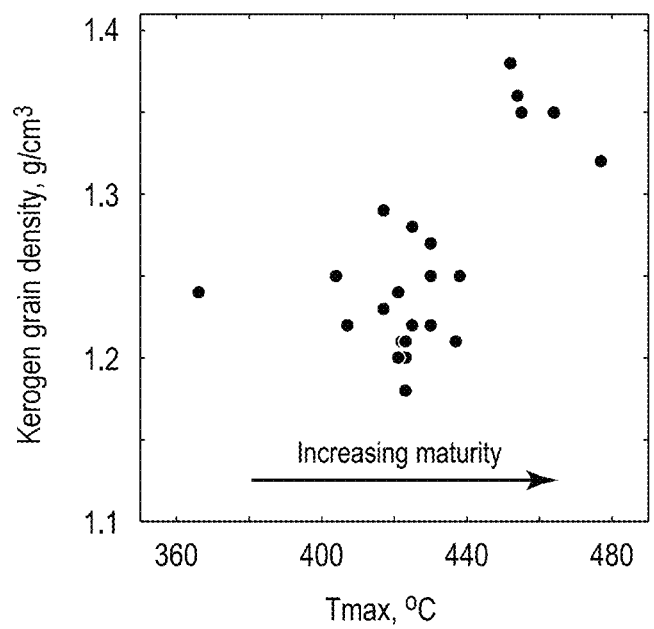
FIGS. 7-8 are graphical representations depicting kerogen density of a formation sample as a function of thermal maturity using differing measuring techniques.
Figure 8:
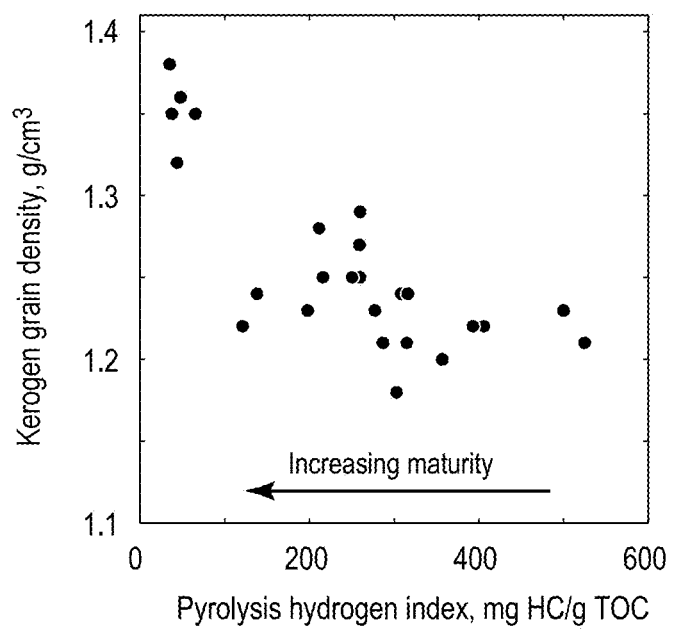

Next, the kerogen density for the samples was estimated as a comparative measurement using other techniques for calculating grain density. With particular respect to FIG. 7, a plot of kerogen grain density of isolated kerogen fractions in Kimmeridge clay formation are shown as a function of thermal maturity indices. $T_{max}$ indicates that kerogen grain density increases during thermal maturation. Similarly, with respect to FIG. 8, the kerogen grain density of isolated kerogen fractions in Kimmeridge clay formation as a function of the hydrogen index (a measure of thermal maturity) obtained from pyrolysis is shown, where the hydrogen index is a measure of the ratio of oil potential in a formation sample compared to the total organic carbon content in the formation sample. However, these methods of determining kerogen grain density require extensive laboratory preparation and may be impractical to conduct in the field and do not relate the kerogen grain density to parameters directly measurable by DRIFTS.

Figure 9:
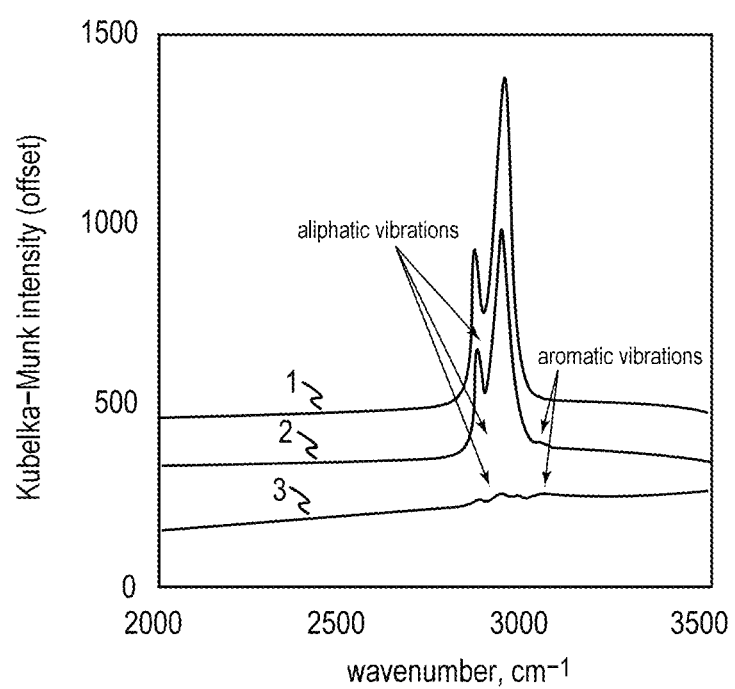
FIG. 9 is a graphical representation depicting the KM intensity of light reflection as a function of wavenumber for various samples of kerogen in accordance with methods of the present disclosure.

The DRIFTS IR measurement was then used to estimate kerogen grain density for the analyzed sample in accordance with methods of the present disclosure. The measurement utilized the direct correlation between DRIFTS IR spectrum lineshape and kerogen grain density. The IR spectrum lineshape and kerogen grain density both respond systematically to variations in kerogen thermal maturity, and the correlation parameters between the IR spectrum lineshape and the kerogen grain density was used to generate the kerogen grain density values for each of the formation samples. With particular respect to FIG. 9, a DRIFTS IR spectrum of three kerogens magnified at the mid-IR range from 2000 cm$^{-1}$ to 3500 cm$^{-1}$ is shown. Because the wavenumbers in this region correspond to the absorbance of various C—H bond vibrations, the spectral intensity at particular wavenumbers in these samples may be used to estimate kerogen concentration, thermal maturity, and grain density by comparing the relative intensity of the absorbance in the aliphatic and aromatic portions of the spectrum.

Figure 10:
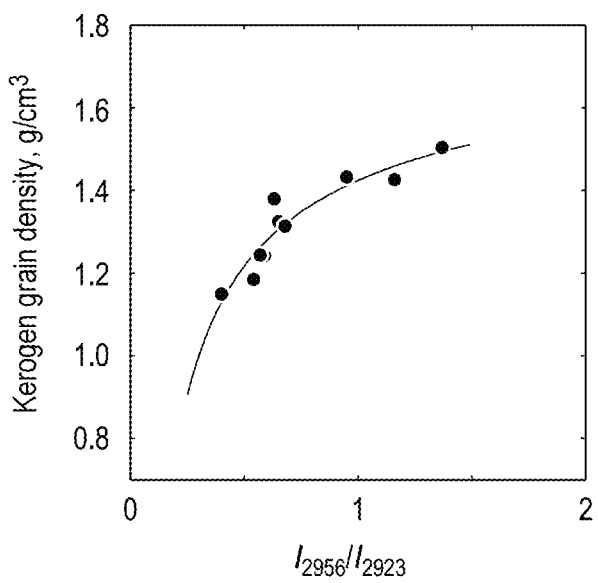
FIG. 10-11 are graphical representations of correlations between kerogen grain density and illustrative IR spectrum lineshape indices in accordance with methods of the present disclosure.
Figure 11:
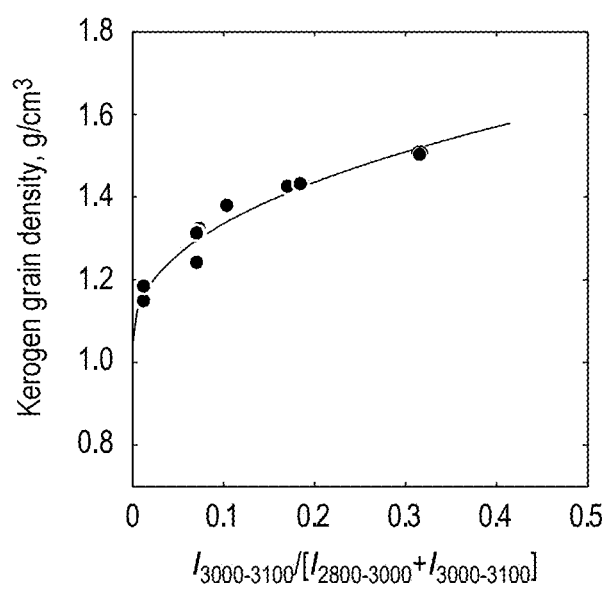
Figure 12:
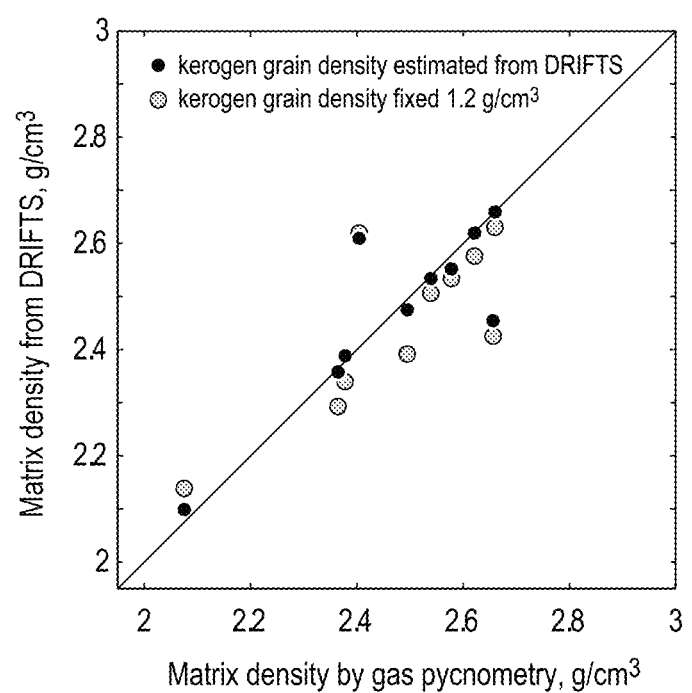
FIG. 12 is a graphical representation showing the comparison of shale matrix density estimated by DRIFTS and determined by gas pycnometry wherein the DRIFTS estimates accounts for variations in kerogen grain density in accordance with methods of the present disclosure.

With particular respect to FIG. 10, the kerogen grain density for a number of samples shown as a function of the ratio of aliphatic CH$_3$ and CH$_2$ band absorbance ($I_{2956}/I_{2923}$), while FIG. 11 shows kerogen grain density of a number of samples as a function of the ratio of aromatic to aliphatic C—H band absorbance ($I_{3000-3100}/[I_{2800-3000}+I_{3000-3100}]$). The grain density of the kerogen component was then computed by fitting the IR spectrum lineshape.

(3) Estimation of Matrix Density.

Matrix density was computed using the inorganic mineralogy and kerogen content from (1), known inorganic mineral grain densities, and kerogen grain density obtained in (2) using the expression for matrix density presented above in Eq. 1. With particular respect to FIG. 11, the matrix density calculated using the DRIFTS analysis is compared against matrix density measured by gas pycnometry.

Figure 13:
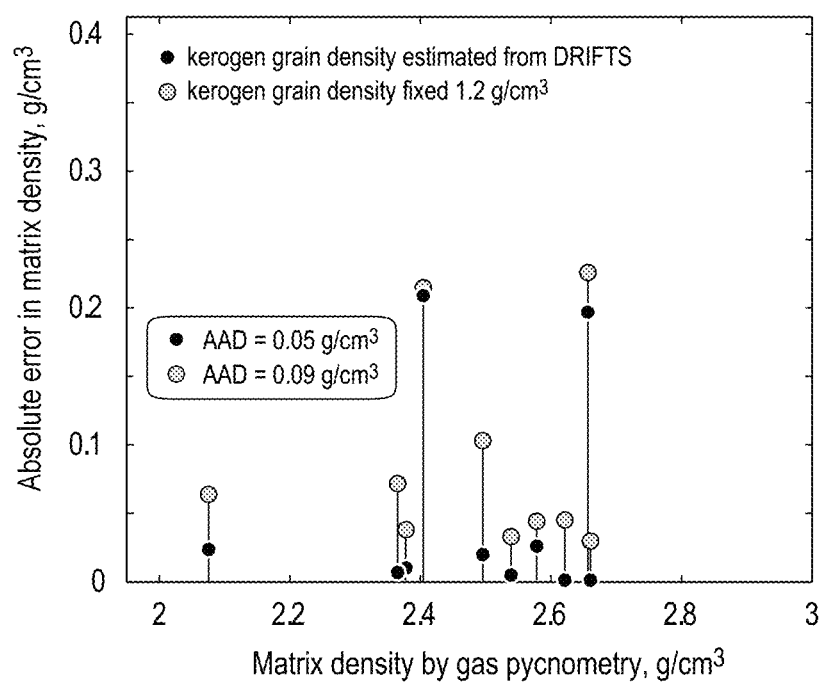
FIG. 13 is a graphical representation showing the absolute error of the measured shale matrix density in accordance with methods of the present disclosure.

The improved accuracy of the matrix density using the calculated kerogen grain density is confirmed in FIG. 13, where data is shown in error form as the absolute difference between the DRIFTS-estimated and measured shale matrix density, and as the calculated value of average absolute deviation (AAD). The matrix density computed using variable kerogen grain density determined from DRIFTS IR is more accurate with an AAD of 0.05 g/cm$^3$ when compared to the same matrix density computed using a fixed kerogen grain density with an AAD of 0.09 g/cm$^3$.

(4) Estimation of Formation Porosity.

Figure 14:
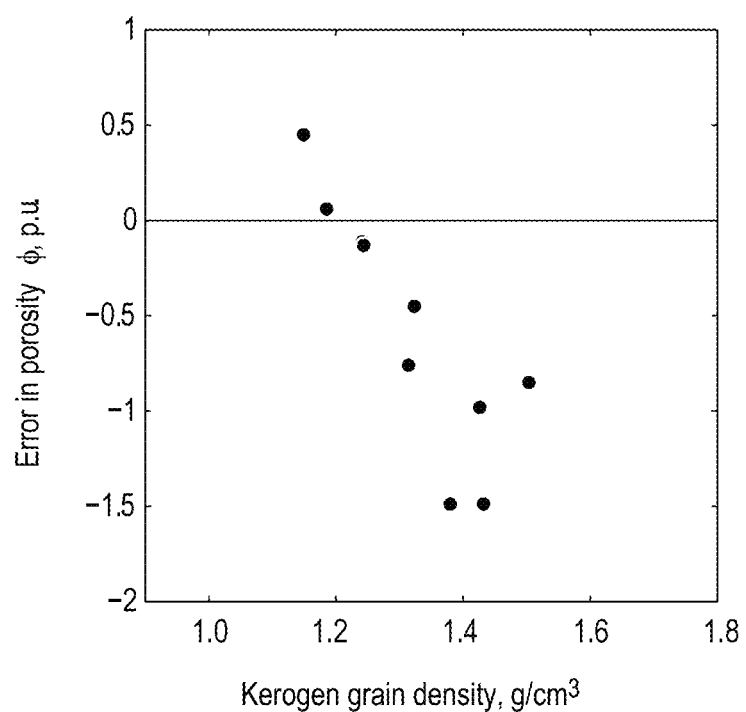
FIG. 14 is a graphical representation showing the error in porosity as a function of porosity using a fixed kerogen grain density of 1.2 g/cm$^3$ instead of the true kerogen grain density estimated in accordance with methods of the present disclosure.

In the next step, formation porosity $\phi$ for the samples was estimated from matrix density using Eq. 3. With particular respect to FIG. 14, the importance of using a kerogen grain density that is estimated directly from thermal maturity, as opposed to a fixed value is illustrated. FIG. 14 plots the hypothetical error (bias) in the estimate of porosity calculated assuming a kerogen grain density of 1.2 g/cm$^3$, instead of the grain density estimated from DRIFTS. The error (y-axis) is plotted as a function of the true kerogen grain density (x-axis). In general, the error in porosity increases as the assumed grain density deviates from the true kerogen grain density. The absolute error may also depend on the kerogen concentration in the formation. FIG. 14 demonstrates that the porosity calculated by assuming a kerogen grain density of 1.2 g/cm³ in this illustration can be in error by 2 p.u. As a practical matter, porosity in thermally-immature formations may be over-estimated if a kerogen grain density of 1.2 g/cm³ is assumed, because the true kerogen density may be lower and kerogen volume greater than assumed.

The DRIFTS data enable the matrix density to be computed on a level-by-level basis without assigning a single matrix density value for the sampled interval or selected zones within the interval.

The porosity estimate obtained using the workflow in accordance with the present disclosure demonstrates significant implications for hydrocarbon reserve estimates because the difference in estimated porosity using the default model and the optimized model can be several porosity units in a source rock that may have less than 5 to 10 percent by volume (vol %) porosity. This difference in the porosity measurement can mean the difference between identifying a formation as a potential reservoir and disregarding the formation as not economically feasible in some cases. Methods in accordance with the present disclosure may also enhance the capabilities of DRIFTS as well as density logging services offered across multiple segments.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method of characterizing a subsurface formation comprising:
   a) performing at least one logging measurement on a sample of the formation that corresponds to a depth in the formation;
   b) performing at least one IR spectroscopy measurement on the sample of the formation that corresponds to the depth in the formation;
   c) determining bulk density at the depth in the formation based on the at least one logging measurement of a);
   d) determining weight fractions of kerogen and inorganic mineral components at the depth in the formation;
   e) determining grain densities of kerogen and the inorganic mineral components at the depth in the formation, wherein the grain density of kerogen is determined by a correlation between grain density of kerogen and IR spectra lineshape data derived from the at least one IR spectroscopy measurement of b);
   f) matrix density at the depth in the formation based on the weight fractions of d) and the grain densities of e); and
   g) determining total porosity at the depth in the formation based on the bulk density of c) and the matrix density of f).

2. The method of claim 1, wherein determining the weight fractions of d) involves analyzing drilling cuttings or core samples.

3. The method of claim 1, wherein determining the weight fractions of d) involves performing one or more diffuse reflectance infrared Fourier transform spectroscopy measurements.

4. The method of claim 1, wherein determining the weight fractions of d) involves using one or more measurements selected from a group consisting of: X-ray diffraction, attenuated total reflection spectroscopy, transmission Fourier transform infrared spectroscopy, X-ray fluorescence, mass spectrometry, LECO combustion analysis, and coulometry.

5. The method of claim 1, further comprising producing a log of the total porosity of the formation as a function of depth.

6. The method of claim 1, further comprising producing hydrocarbons from the subsurface formation.

7. The method of claim 1, wherein the at least one IR spectroscopy measurement of b) comprises at least one diffuse reflectance infrared Fourier transform spectroscopy measurement.

8. The method of claim 1, wherein the grain density of kerogen is determined in e) by a correlation between grain density of kerogen and a ratio of IR lineshapes derived from the at least one IR spectroscopy measurement of b), wherein the ratio of IR lineshapes involves at least one of the total aliphatic C—H IR absorbance between 2800 and 3000 cm⁴ and the total aromatic C—H IR absorbance between 3000 and 3100 cm'.

9. The method of claim 1, wherein the grain density of kerogen is determined in e) by a correlation between grain density of kerogen and a ratio of IR lineshapes derived from the at least one IR spectroscopy measurement of b), wherein the ratio of IR lineshapes involves at least one of the symmetric $CH_3$ and $CH_2$ stretches at wavenumbers centered around 2857 and 2872 $cm^{-1}$, or the asymmetric $CH_3$ and $CH_2$ stretches at wavenumbers centered around 2957 $cm^{-1}$ and 2925 $cm^{-1}$.

10. The method of claim 1, wherein the at least one logging measurement of a) utilizes a wellbore tool selected from a group consisting of: wireline, logging-while-drilling, and openhole through-the-bit technologies.

11. The method of claim 1, wherein the at least one logging measurement of a) is selected from the group consisting of: density logging, conductivity measurements, and nuclear magnetic resonance logging.

12. The method of claim 1, wherein the at least one logging measurement of a) involves obtaining seismic or acoustic data.

13. The method of claim 1, wherein determining the bulk density of c) involves constructing a synthetic bulk density log from drill cuttings or core samples.

14. The method of claim 1, wherein the matrix density of f) is depth correlated to a bulk density log using one or more of gamma ray measurements or wellbore tool logs.

15. The method of claim 1, wherein the grain density of kerogen is determined in e) by constructing IR spectra lineshape data derived from the at least one IR spectroscopy measurement of b).

16. The method of claim 1, wherein the at least one IR spectroscopy measurement of b) employs attenuated total reflection spectroscopy or transmission Fourier transform infrared spectroscopy.

17. The method of claim 1, wherein the matrix density of f) is computed as a sum of mineral concentrations weighted by their respective grain densities.

18. The method of claim 1, wherein the total porosity of g) is determined from the bulk density of c), the matrix density of f), and a bulk fluid density.

19. The method of claim 18, wherein the bulk fluid density is an assumed value or an estimated value derived from local calibration measurements or other techniques.

20. The method of claim 18, wherein the total porosity of g) is determined according to the following relation:

$$f_T = \frac{r_{ma} - r_{bulk}}{r_{ma} - r_{fluid}},$$

where $f_T$ is the total porosity of g), $r_{bulk}$ is the bulk density of c), $r_{ma}$ is the matrix density of f), and $r_{fluid}$ is the bulk fluid density.

21. The method of claim 1, wherein the IR spectra lineshape data comprises a ratio of IR lineshapes derived from the at least one IR spectroscopy measurement of b).

* * * * *